(12) United States Patent
Iriyama (10) Patent No.: US 8,102,415 B2
(45) Date of Patent: Jan. 24, 2012

(54) ELECTRONIC ENDOSCOPE SYSTEM AND PROCESSOR FOR ELECTRONIC ENDOSCOPE

(75) Inventor: Noriko Iriyama, Saitama (JP)

(73) Assignee: Hoya Corporation, Tokyo (JP)

( * ) Notice: Subject to any disclaimer, the term of this patent is extended or adjusted under 35 U.S.C. 154(b) by 1036 days.

(21) Appl. No.: 12/019,028

(22) Filed: Jan. 24, 2008

(65) Prior Publication Data

US 2008/0198223 A1 Aug. 21, 2008

(30) Foreign Application Priority Data

Feb. 19, 2007 (JP) .................................. 2007-037617

(51) Int. Cl.
*A62B 1/04* (2006.01)
*H04N 13/00* (2006.01)

(52) U.S. Cl. .......................................... 348/65; 348/45

(58) Field of Classification Search .............. 348/45, 348/46, 61, 72, 77, 79; 600/36, 120, 126, 600/132, 156, 920; 396/17
See application file for complete search history.

(56) References Cited

U.S. PATENT DOCUMENTS

| | | | | |
|---|---|---|---|---|
| 5,902,230 | A * | 5/1999 | Takahashi et al. | 600/109 |
| 6,876,347 | B2 * | 4/2005 | Tashiro et al. | 345/87 |
| 6,881,188 | B2 * | 4/2005 | Furuya et al. | 600/158 |
| 2001/0002842 | A1 * | 6/2001 | Ozawa | 348/45 |
| 2002/0093563 | A1 * | 7/2002 | Cline et al. | 348/65 |
| 2002/0126204 | A1 | 9/2002 | Takeshige et al. | |
| 2003/0046562 | A1 * | 3/2003 | Uchikubo | 713/189 |
| 2005/0222499 | A1 * | 10/2005 | Banik et al. | 600/132 |
| 2007/0041720 | A1 * | 2/2007 | Iketani | 396/17 |
| 2007/0106121 | A1 * | 5/2007 | Yokota et al. | 600/188 |
| 2007/0106122 | A1 * | 5/2007 | Yokota et al. | 600/188 |
| 2007/0149851 | A1 * | 6/2007 | Nakamura et al. | 600/129 |
| 2008/0018734 | A1 | 1/2008 | Iriyama | |
| 2008/0027286 | A1 * | 1/2008 | Xie | 600/181 |
| 2009/0027486 | A1 * | 1/2009 | Hirakawa et al. | 348/45 |

FOREIGN PATENT DOCUMENTS

JP 2002-263063 9/2002

* cited by examiner

*Primary Examiner* — Ario Etienne
*Assistant Examiner* — Sargon Nano
(74) *Attorney, Agent, or Firm* — Greenblum & Bernstein, P.L.C.

(57) ABSTRACT

An electronic endoscope system includes an electronic endoscope, a processor connected with the electronic endoscope, and a server that performs data communication with the processor via a network. The processor sends, to the server, update request data including an adjusted image and positional information of an adjusted area in the adjusted image. Further the processor receives, from the server, updating data created based on the update request data, and updates at least one of image processing tools used by the electronic endoscope and processor based on the updating data.

17 Claims, 4 Drawing Sheets

ELECTRONIC ENDOSCOPE SYSTEM AND PROCESSOR FOR ELECTRONIC ENDOSCOPE

BACKGROUND OF THE INVENTION

The following description relates to an electronic endoscope system provided with a processor for an electronic endoscope, which processor is connectable with a predetermined network and configured to process video picture taken by the electronic endoscope, and a server configured to perform data communication with the electronic endoscope via the predetermined network.

An electronic endoscope, which is provided with an imaging device such as a CCD (Charge Coupled Device) at a distal end portion thereof, is configured such that an image taken by the imaging device is displayed on a monitor. In such a configuration, the electronic endoscope is linked with a processor for an electronic endoscope (hereinafter, referred to as an electronic endoscope processor) which is configured to process a picture signal from the electronic endoscope and convert the processed signal into a predetermined format of video signal (such as an NTSC video signal and RGB signal based on VESA standards), and transmit the converted signal to the monitor.

The electronic endoscope processor does not only convert an image outputted as a picture signal from the electronic endoscope into a video signal, but also performs predetermined image processing (e.g., white balance adjustment, γ correction, and noise reduction) for the image or superimposes a predetermined character string onto the image. In addition, along with such a trend that the electronic endoscope processor is improved to be more multifunctional, there has been proposed an electronic endoscope processor provided with an operation menu to which a GUI (Graphical User Interface) is applied.

In such an electronic endoscope processor, for the sake of improvement of an image processing function (e.g., improvement of an image processing routine and addition of a new image processing function) and/or improvement of an operability of the operation menu, various programs to be executed by the electronic endoscope processor are desired to be updatable. Therefore, as disclosed in Japanese Patent Provisional Publication No. 2002-263063 (hereinafter, referred to as '063 Publication), there has been proposed an electronic endoscope processor configured to be connectable with a server via a predetermined network and receive updating data from the server so as to update a program and the like.

However, such a conventional configuration disclosed in '063 Publication is merely designed such that updating software is automatically downloaded into the electronic endoscope processor. The conventional configuration is effective in the case where respective pieces of software for two or more electronic endoscope processors of the same model are concurrently updated. Yet, recently, there has been desired such a configuration that a program and parameters used in the program that are customized to meet user's requirements can be utilized in the electronic endoscope processor.

Further, along with a trend that the imaging device is improved to be higher-integrated and more sophisticated, there is coming into use such a configuration that a primary signal processing circuit processing an output signal of the imaging device is incorporated into the electronic endoscope. For example, in an electronic endoscope that uses a color CCD as the imaging device, the primary signal processing circuit executes a signal processing program with parameters conforming to arrangement and characteristics of color filters provided on an imaging surface of the CCD. The program and parameters are appropriately configured depending on the arrangement and characteristics of the color filters before shipping, yet are not configurable by a user after purchase. However, in the same manner as the electronic endoscope processor, the program and parameters are desired to be replaceable with a program and parameters customized to meet the user's requirements.

SUMMARY OF THE INVENTION

The present invention is advantageous in that there can be provided an improved electronic endoscope system and processor for the electronic endoscope that make it possible to customize a program that runs in the processor or electronic endoscope and parameters used in the program so as to meet user's requirements.

According to an aspect of the present invention, there is provided an electronic endoscope system, which includes an electronic endoscope configured to process an image captured thereby so as to generate a first image with a first image processing tool, a network, a processor for the electronic endoscope connected with the electronic endoscope and network, the processor being configured to process the first image generated by the electronic endoscope, and a server configured to perform data communication with the processor via the network. The processor for the electronic endoscope includes an area specifying unit configured to specify an area to be adjusted in the first image generated by the electronic endoscope, an image adjustment unit configured to provide image adjustment for the area in the first image that is specified by the area specifying unit so as to generate a second image with a second image processing tool, a request creating unit configured to create update request data including the second image data and positional information representing a position of the specified area in the first image, a request sending unit configured to send, to the server, the update request data created by the request creating unit, an updating data receiving unit configured to receive, from the server, updating data for updating at least one of the first and second image processing tools, and an updating unit configured to update at least one of the first and second image processing tools based on the updating data received by the updating data receiving unit. The server includes a request receiving unit configured to receive the update request data sent by the request sending unit, and an updating data sending unit configured to send, to the processor, the updating data created based on the update request data received by the request receiving unit.

Optionally, the processor may further include a display unit, a first display control unit configured to control the display unit to display thereon the first image generated by the electronic endoscope, and a second display control unit configured to control the display unit to display thereon the second image generated by the image adjustment unit.

Optionally, the processor may further include an input unit configured to accept an external input. In this case, the area specifying unit may specify the area to be adjusted in the first image based on the external input accepted by the input unit.

Optionally, the processor may further include an input unit configured to accept data inputted therethrough. In this case, the image adjustment unit may provide the image adjustment for the specified area in the first image based on the data inputted through the input unit.

Further optionally, the area specifying unit may specify a plurality of areas to be adjusted in the first image. In this case, the image adjustment unit may provide different image adjustments for the plurality of areas in the first image that are specified by the area specifying unit, respectively.

Optionally, the first image processing tool may include a program and parameter employed in the program that are used by the electronic endoscope, and further, the second image processing tool may include a program and parameter employed in the program that are used by the image adjustment unit of the processor.

Still optionally, the processor may further include a textual information input unit configured to accept an input of textual information. In this case, the update request data may include the textual information accepted by the textual information input unit.

Optionally, the network may include an Internet.

Optionally, the processor may further include a certification information input unit configured to accept an input of certification information, a certificate information sending unit configured to send the certification information accepted by the certification information input unit, before the request sending unit sends the update request data, and a success notification receiving unit configured to receive, from the server, a successful certification notification issued when certification with the certification information sent by the certification information sending unit is successful. In this case, the server may further include a certification information receiving unit configured to receive the certificate information sent by the certificate information sending unit of the processor, a certificating unit configured to implement the certification with the certification information received by the certification information receiving unit, and a success notification issuing unit configured to issue, to the processor, the successful certification notification when the certification with the certification information received by the certification information receiving unit is successful. Further, the request sending unit of the processor may send the update request data to the server in response to receiving the successful certification notification.

According to another aspect of the present invention, there is provided a processor for an electronic endoscope, which is connectable with the electronic endoscope and configured to perform data communication with an external device via a network, the processor including an area specifying unit configured to specify an area to be adjusted in a first image generated with a first image processing tool by the electronic endoscope, an image adjustment unit configured to provide image adjustment for the area in the first image that is specified by the area specifying unit so as to generate a second image with a second image processing tool, a request creating unit configured to create update request data including the second image data and positional information representing a position of the specified area in the first image, a request sending unit configured to send, to the external device, the update request data created by the request creating unit, an updating data receiving unit configured to receive, from the external device, updating data for updating at least one of the first and second image processing tools, and an updating unit configured to update at least one of the first and second image processing tools based on the updating data received by the updating data receiving unit.

DETAILED DESCRIPTION OF THE EMBODIMENTS

Figure 1:
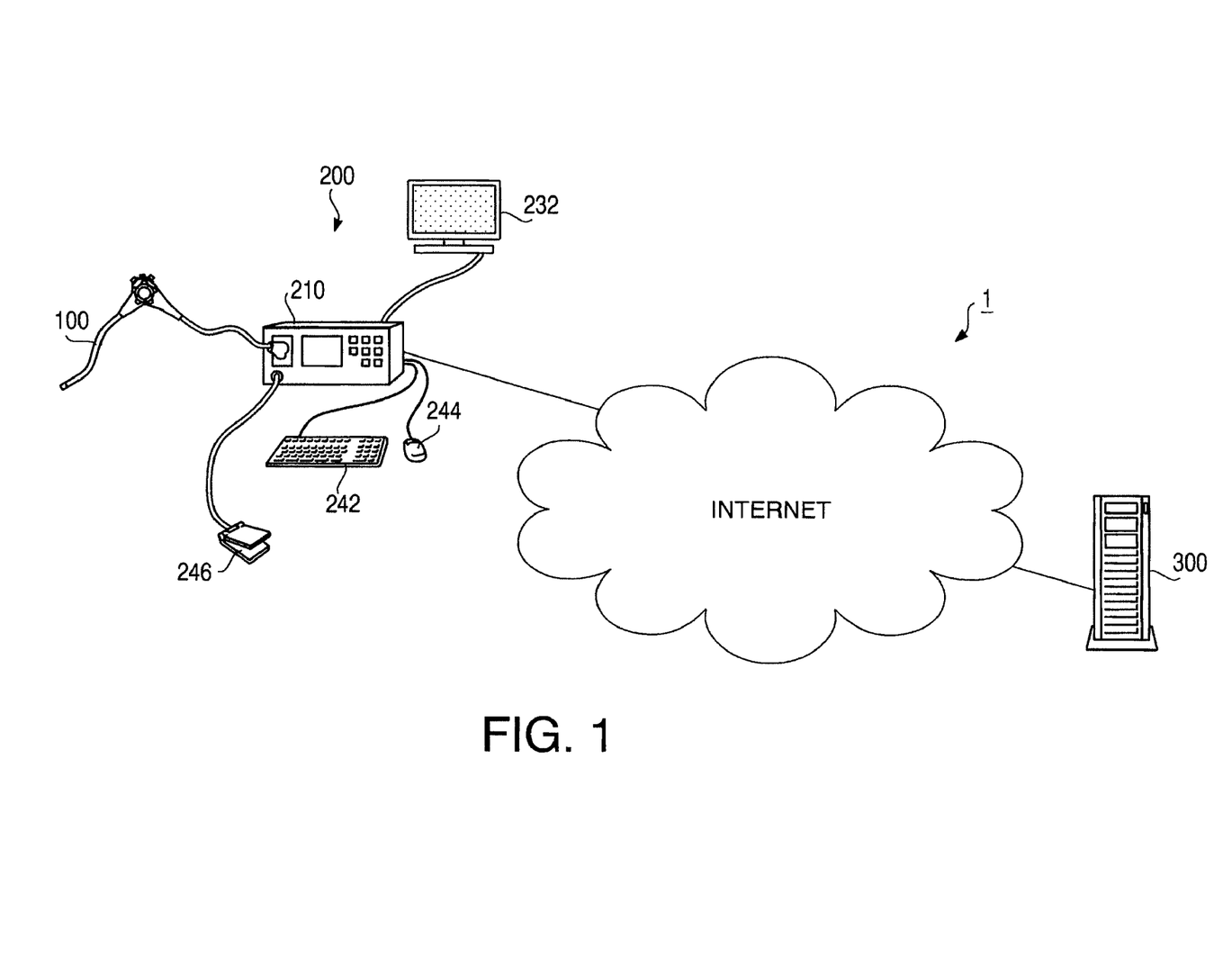
FIG. 1 schematically shows an overall configuration of an electronic endoscope system in an embodiment according to one or more aspects of the present invention.

Hereinafter, an embodiment according to aspects of the present invention will be described with reference to the accompanying drawings. FIG. 1 schematically shows an overall configuration of an electronic endoscope system in the present embodiment. In the present embodiment, a program and parameters for controlling an electronic endoscope processor 200 and electronic endoscope 100 can be obtained from a server 300 via an Internet.

A processor main body 210 of the electronic endoscope processor 200 is connected with the electronic endoscope 100. The processor main body 210 has a function of a light source that supplies illuminating light to a light guide 106 (see FIG. 2) of the electronic endoscope 100, and a function of a video processor that processes a picture signal from a CCD incorporated in the electronic endoscope and causes a monitors to display thereon the processed picture signal. In addition, there are connected with the processor main body 210, input means, which is used when a user operates the electronic endoscope 100 and electronic endoscope processor 200, such as a keyboard 242, mouse 244, and footswitch 246. It is noted that, a single pair of the electronic endoscope 100 and electronic endoscope processor 200 is shown in FIG. 1, actually, two or more pairs of the electronic endoscope 100 and electronic endoscope processor 200 are connectable with the server 300 via the Internet.

Figure 2:
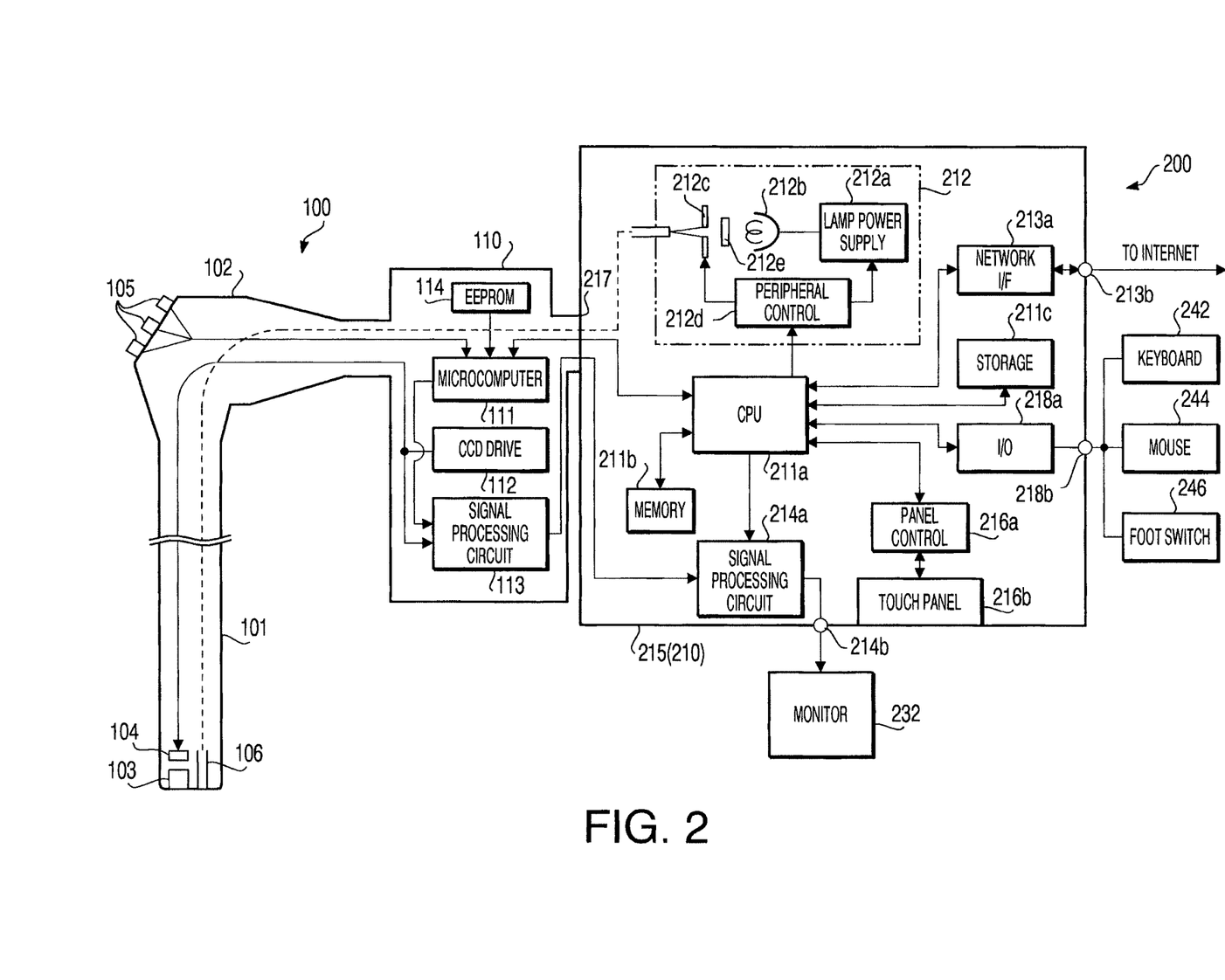
FIG. 2 is a block diagram schematically showing electrical configurations of an electronic endoscope 100 and a processor for the electronic endoscope in the embodiment according to one or more aspects of the present invention.

FIG. 2 is a block diagram schematically showing electrical configurations of the electronic endoscope 100 and electronic endoscope processor 200. The processor main body 210 is configured with various devices being connected thereto inside a housing 215 of the electronic endoscope processor 200 and on an outer face of the housing 215. A connector 217 is provided on the outer face of the housing 215, and connected with a connector portion 110 of the electronic endoscope 100. When the electronic endoscope 100 is connected to the processor main body 210, it becomes possible to supply illuminating light from the electronic endoscope processor 200 to the light guide 106. In addition, it is possible for the electronic endoscope processor 200 to acquire an image converged onto a light receiving surface of the CCD 104 as a picture signal with an imaging optical system 101 of the electronic endoscope 100.

Firstly, a function as a light source of the electronic endoscope processor 200 will be described. A light source unit 212 is incorporated in the housing 215. The light source unit 212 includes a lamp 212b for generating the illuminating light, lamp power supply 212a that drives the lamp 212b, converging lens 212e that makes the illuminating light generated by the lamp 212b incident onto an incidence end face of the light guide 106, aperture 212c that adjusts an intensity of the illuminating light to be incident onto the incidence end face of the light guide 106, and peripheral control 212*d* that controls the lamp power supply 212*a* and aperture 212*c*. The peripheral control 212*d* is controlled by a CPU 211*a* of the processor main body 210. Therefore, the CPU 211*a* can turn ON/OFF the illuminating light to be incident to the light guide 106 and adjust the intensity of the illuminating light by controlling the peripheral control 212*d*. It is noted that a light intensity sensor (not shown) is provided between the aperture 212*c* and the incidence end face of the light guide 106. The CPU 211*a* can adjust the light intensity to be equivalent to a desired value through a feedback control with an output of the light intensity sensor.

Subsequently, processing of a video picture taken by the electronic endoscope 100 will be described. The connector portion 110 of the electronic endoscope 100 is provided with a CCD drive circuit 112. The CCD drive circuit 112 is linked with the CCD 104 via a cable. The CCD drive circuit 112 generates a pulse for driving the CCD 104, and sends the generated pulse to the CCD 104, so as to drive the CCD 104. In addition, the connector portion 110 is provided with a signal processing circuit 113, which processes a CCD signal outputted from the CCD 104 to generate a picture signal. The generated picture signal is transmitted to a signal processing circuit 214*a* incorporated inside the processor main body 210 of the electronic endoscope processor 200. It is noted that the CCD drive circuit 112 and signal processing circuit 113 are controlled by a microcomputer 111, which is controlled by the CPU 211*a*, embedded in the connector portion 110 of the electronic endoscope 100. Accordingly, from the electronic endoscope processor 200 side, the CCD drive circuit 112 and signal processing circuit 113 can be controlled via the microcomputer 111. The control of the CCD drive circuit 112 and signal processing circuit 113 by the microcomputer 111 is carried out with a program of an EEPROM 114 embedded in the connector portion 110 being executed by the microcomputer 111. Further, the signal processing circuit 113 is provided with a kind of DSP (Digital Signal Processor). Digital signal processing by the DSP is performed with a predetermined program being executed by the DSP. The program and parameters to be used in the program are stored in the EEPROM 114. When driving the DSP, the microcomputer 111 reads out the program and the parameters from the EEPROM 114, and transmits them to the DSP such that the DSP executes the program.

The signal processing circuit 214*a* in the processor main body 210 performs predetermined image processing (e.g., adjustments of brightness, contrast, and color balance) for an image obtained from the received picture signal, and superimposes predetermined textual information onto the obtained image. Furthermore, the signal processing circuit 214*a* converts the processed image into a predetermined format of video signal (e.g., an RGB signal based on VESA standards), and transmits the video signal to a monitor joining connector 214*b* provided on the outer face of the housing 215. Therefore, by connecting a monitor 232 to the monitor joining connector 214*b*, the image taken by the electronic endoscope 100 can be displayed on the monitor 232. The aforementioned image processing and superimposing the textual information are implemented with the signal processing circuit 214*a* being controlled by the CPU 211*a*.

It is noted that the CCD 104 captures a single image at predetermined time intervals (e.g., 1/30 seconds). Hence, a video picture around a distal end portion of an insertion tube 101 of the electronic endoscope 100 is displayed as a motion picture on the monitor 232.

Next, configurations of various input means such as the keyboard 242, the mouse 244, the footswitch 246, a touch panel 216*b*, and operation buttons 105 of the electronic endoscope 100 will be explained. An I/O port 218*b* is provided on the outer face of the housing 215 of the processor main body 210. The keyboard 242, the mouse 244, and the footswitch 246 are joined with the processor main body 210 via the I/O port 218*b*. The CPU 211*a* can acquire data inputted through the keyboard 242, the mouse 244, and the footswitch 246 by controlling an I/O controller 218*a* incorporated in the housing 215.

In addition, the touch panel 216*b* is provided on the outer face of the housing 215. The touch panel 216*b* is configured with an LCD monitor and a touch sensor panel being combined together. For example, an image representing an operating member such as a button is displayed in a predetermined position (coordinates) on the LCD monitor (touch panel), and a user of the electronic endoscope system 1 can operate the electronic endoscope processor 200 by touching the predetermined position on the touch panel. A panel control circuit 216*a* is provided inside the processor main body 210. The CPU 211*a* can cause the touch panel 216*b* to display thereon a desired image, or detect the coordinates of a position on the touch sensor panel that is touched by the user by controlling the panel control circuit 216*a*.

Additionally, the microcomputer 111 of the electronic endoscope 100 is connected with operating the buttons 105 provided at a handle 102 of the electronic endoscope 100. The CPU 211*a* of the processor main body 210 can detect an ON/OFF state of each operating button 105 via the microcomputer 111.

The aforementioned various functions of the electronic endoscope processor 200, such as the image processing and the operation of superimposing the textual information with the signal processing circuit 214*a*, and operations through the various input means (operation of inputting textual information displayed on the monitor 232 through the keyboard 242), are achieved with a predetermined program stored in a storage 211*c* being read out and executed by the CPU 211*a*. It is noted that a memory 211*b* is used as a working area when the CPU 211*a* executes the predetermined program.

Furthermore, a network cable connector 213*b* is provided on the outer face of the housing 215 of the processor main body 210, and is configured to be connectable with a predetermined network cable. There is incorporated in the processor main body 210, a network interface circuit 213*a* for performing data communication with a host (for instance, server 300 shown in FIG. 1) on the Internet via the network cable. The CPU 211*a* controls the network interface circuit 213*a* so as to receive data from the server 300 or transmits data to the server 300.

In the present embodiment, by downloading updating data from the server 300, the processor main body 210 can update a program to be executed by the CPU 211*a*, the microcomputer 111 of the electronic endoscope 100, or the signal processing circuit 113, and parameters used in the program. Hereinafter, a configuration for attaining the above operations will be described.

Firstly, a procedure of updating a program of the electronic endoscope processor 200 in the present embodiment will be explained. In order to update the program, the user firstly carries out a predetermined operation (for example, pressing a specific key of the keyboard 242) to connect the electronic endoscope processor 200 to the server 300. Then, data for a log-in screen image are transmitted to the electronic endoscope processor 200. The electronic endoscope processor 200 analyzes the data, and causes a log-in screen image as shown in FIG. 3 to be displayed on the monitor 232.

Figure 3:
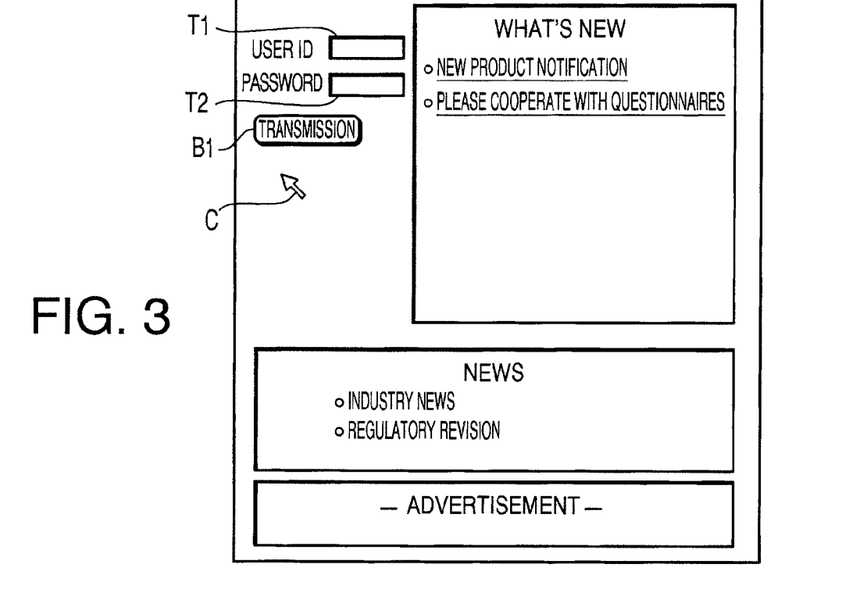
FIG. 3 is an example of a log-in screen image in the embodiment according to one or more aspects of the present invention.

As shown in FIG. 3, there are displayed on the log-in screen image, an ID input area T1 for inputting a user ID thereinto, password input area T2 for inputting a user password thereinto, and transmission button B1 for sending the inputted ID and password to the server 300. In addition, there are displayed on the log-in screen image, news related to the electronic endoscope, an advertisement from a company administrating the server 300, and a link for answering a questionnaire.

The user operates the keyboard 242 and inputs the user ID and user password into the ID input area T1 and password input area T2, respectively. It is noted that the user ID and user password are given by the company administrating the server 300 when the user purchases the electronic endoscope processor. Subsequently, the user operates the mouse 244 (see FIG. 2) to put a cursor on the button B1, and clicks a button of the mouse 244. Thereby, the user ID and user password are transmitted to the server 300. It is noted that the user ID and user password may preferably be encrypted and transmitted.

Figure 4:
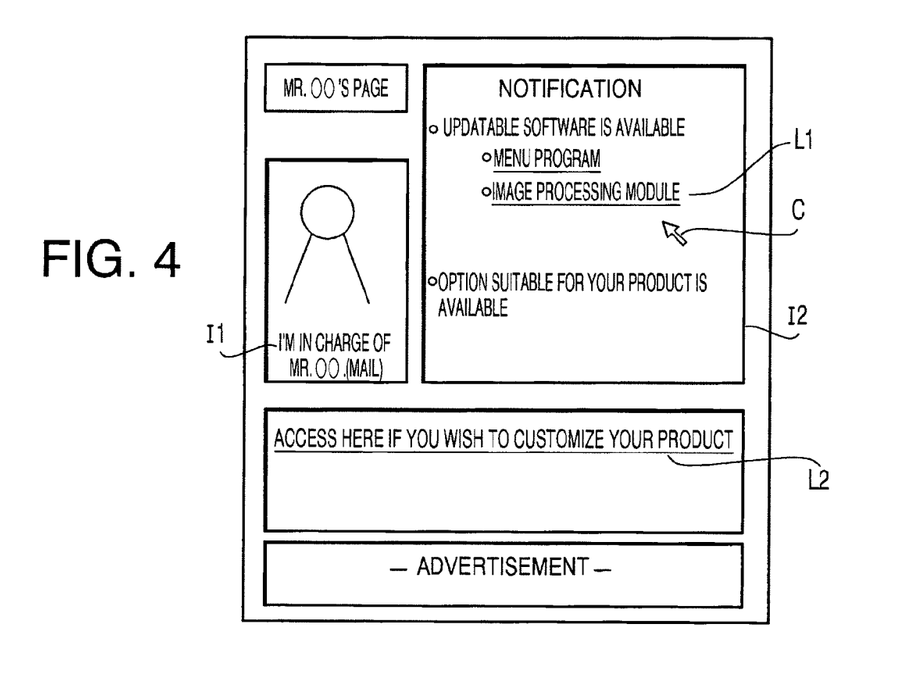
FIG. 4 is an example of a user screen image in the embodiment according to one or more aspects of the present invention.

When receiving the user ID and user password from the electronic endoscope processor 200, the server 300 performs user certification with the user ID and user password. When succeeding in the user certification, the server 300 creates data of a user screen image and sends it to the electronic endoscope processor 200. When receiving the created data, the electronic endoscope processor 200 develops the data to display a user screen image as shown in FIG. 4 on the monitor 232.

On the user screen image, there are arranged a CE information display area I1 in which there is displayed information regarding a customer engineer who is in charge of the user (such as an engineer's name, photograph of an engineer's face, and engineer's mail address) and a notification display area I2 in which there is displayed notification for the user. In the notification display area I2, there is displayed a link L1 to the updating data for software used in the electronic endoscope processor 200. When the user wishes to update the software, the user clicks the link L1 with the mouse 244. Thereby, a request is transmitted to the server 300. The server, which has received the request, sends the updating data corresponding to the link L1 to the electronic endoscope processor 200, and updates the software. It is noted that the server 300 can send a document and/or tutorial program for letting the user understand what is to be updated, prior to sending the updating data to the electronic endoscope processor. The user can grasp what is to be updated by reading the document or running the tutorial program.

In the present embodiment, when the user of the electronic endoscope processor 200 operates a predetermined input means (for example, presses a predetermined key of the keyboard 242 shown in FIG. 2), a program for downloading an updating program is executed. When the updating program is downloaded, the CPU 211a of the electronic endoscope processor 200 executes the updating program downloaded. When the updating program is executed, the program and parameters stored in the storage 211c are updated. Meanwhile, when the updating program is configured to update a program and parameters for the microcomputer 111 of the electronic endoscope 100 or signal processing circuit 113, the CPU 211a controls the microcomputer 111 to update the program and parameters stored in the EEPROM 114.

Figure 5:
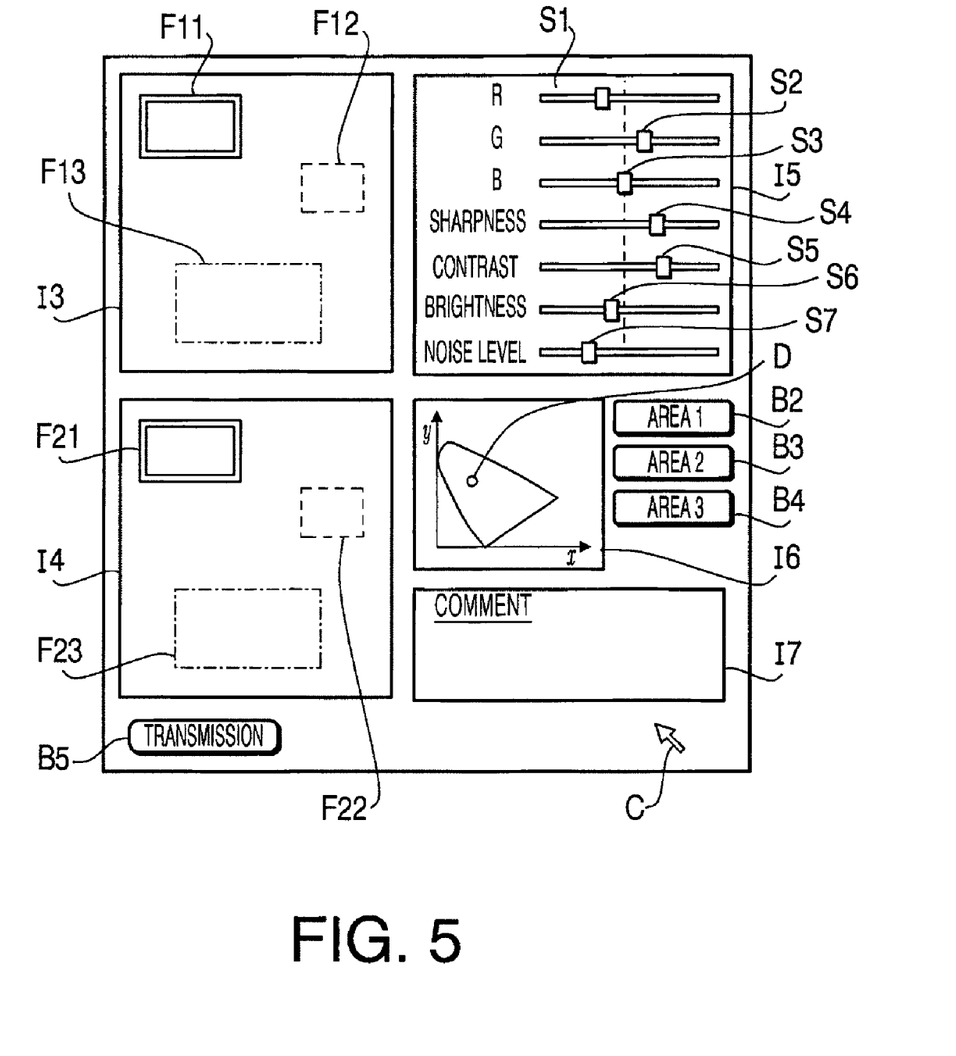
FIG. 5 is an example of a customizing screen image in the embodiment according to one or more aspects of the present invention.

In addition, there is displayed in the user screen image, a link L2 to a customizing request accepting page for accepting a request for customizing software. When the user wishes to customize the software, the user clicks the link L2 with the mouse 244. Thereby, the CPU 211a controls the signal processing circuit 214a to display a customizing screen image as shown in FIG. 5 on the monitor 232.

In the customizing screen image, there are arranged in a vertical direction, a first image display area I3 in which a first image taken by the electronic endoscope 100 is displayed, and a second image display area I4 in which there is displayed a second image obtained by processing the first image with a below-mentioned image adjusting operation. The first and second images are still images, which are previously acquired by the user of the electronic endoscope processor 200 and stored in the storage 211c. Therefore, the first and second images are read out from the storage 211c as required, and then used. It is noted that the second image is the same as the first image before performing the image adjustment, and modified by the image adjustment. Hence, the user can check a result of the image adjustment by comparing the first and second images.

At a right side of the first image display area I3, there is located an image adjusting tool display area I5, in which a plurality of sliders S1 to S7 (seven sliders in FIG. 5) are arranged. The user of the electronic endoscope processor 200 (see FIG. 2) can adjust an image in a below-mentioned predetermined area in the first image by operating the mouse 244 (see FIG. 2) to move the sliders S1 to S7. Specifically, the user puts the cursor C on any one of the sliders S1 to S7, and moves the cursor C in a horizontal direction by laterally moving the mouse 244 with the button of the mouse 244 being pressed (drag operation). Then, the slider is moved following the cursor C. When the cursor C is placed in a desired position, the user takes his finger off the button of the mouse 244 to determine the location of the slider. Then, the image adjustments are performed depending on the locations of the sliders S1 to S7, respectively. For example, the uppermost slider S1 is configured to adjust a red (R) component of the image. When the slider S1 is shifted right, the red component in an area of the second image that corresponds to the predetermined area of the first image is heightened. Meanwhile, when the slider S1 is shifted left, the red component in the area of the second image is diminished. In the same manner, the other sliders S2 to S7 are configured to adjust a green (G) component, blue (B) component, sharpness, contrast, brightness, and permissible noise level, respectively.

Beneath the image adjusting tool display area I5, there are arranged a color space graph display area I6, and first to third area selecting buttons B2 to B4. The first and third area selecting buttons B2 to B4 are used for specifying a subject area of the aforementioned image adjustment. For example, the user puts the cursor C on the first selecting button B2 and presses the button of the mouse (see FIG. 2). Next, the user operates the mouse 244 and specifies any two points in the first image display area I3 (or the second image display area I4) (for example, puts the cursor C on a point and presses the button of the mouse 244, and thereafter, puts the cursor C on another point and presses the button of the mouse 244). Thereby, a rectangle area with opposing corners defined by the specified two points is specified as a first area. At this time, in the first and second images, frames F11 and F21 defining the first area are displayed, respectively. Here, a relative location of the frame F11 with respect to the first image is equivalent to that of the frame F21 with respect to the second image. In the same manner, by operating the second and third selecting buttons B3 and B4, it is possible to specify a second area and third area, respectively. The second areas are defined by frames F12 and F22 in the first and second images, respectively. Further, the third areas are defined by frames F13 and F23 in the first and second images, respectively. It is noted that, after the first to third areas are specified once, the areas are held. For example, even though, after specifying the first area, the second area is specified, and then the first area selecting button B2 is operated again, the first area specified earlier is not cleared.

The first to third area selecting buttons B2 to B4 are used not only for specifying the first to third areas but also for selecting for which area the image adjustment is to be performed among the specified first to third areas. Specifically, when an area selecting button that corresponds to an area for which the image adjustment is desired to be performed is operated, the area corresponding to the button is set to be active. After that, the image adjustment can be performed for the active area until any of the other area selecting buttons is pressed. It is noted that frames and a button that correspond to an active area are displayed in fashions different from the other frames and buttons, respectively. For example, in FIG. 5, the frames F11 and F21 corresponding to the first area, which is currently active, are drawn by double lines. In addition, each of the second and third area selecting buttons B3 and B4 is drawn with a darker bottom end and right end thereof so as to appear to be protruded from a background. On the contrary, the first area selecting button B2 is drawn with a darker top end and left end thereof so as to appear to be recessed from the background.

In the color space graph display area I6, a color space graph is displayed. The color space graph is configured to visually show where an average color in an active area in the second image is located in color space coordinates. In FIG. 5, the first area is active. Accordingly, color space coordinates of an average color in the first area of the second image is indicated as a point D in the color space graph. When the average color in the active area of the second image is changed due to the image adjustment, the point D is also shifted in the color space graph. Therefore, the user can clearly understand what change is caused by the image adjustment. Further, the color space graph used in the present embodiment conforms to a Yxy color space coordinate system. However, color space graphs conforming to other color space coordinate systems, such as an L*a*b color space and chromaticity diagram, may be employed. Further, such a configuration that a color space graph to be used can be selected from a plurality of color space graphs may be possible.

At a lower left side of the customizing screen image, a transmission button B5 is placed. By operating the mouse 244 (see FIG. 2) to put the cursor C on the transmission button B5, and pressing the button of the mouse 244, image data of the first and second images and update request data including coordinate data of specified opposing corners of the first to third areas are created by the CPU 211a. Subsequently, the CPU 211a controls the network interface 213a to send the image data of the first and second images and update request data to the server 300 (see FIG. 1). The update request data are sent to a developer of the program of the electronic endoscope 100 or electronic endoscope processor 200 via the server 300. The developer compares data of the first and second images. Based on the comparison result, the developer creates an updating program for updating the program and parameters, and sends the created program and parameters to the server 300. Consequently, the link L1 to the updating program is displayed in the notification display area I2 on the user screen image (see FIG. 4). The user can acquire the updating program by clicking the link L1 with the mouse 244.

Further, in the customizing screen image in FIG. 5, a comment input area I7 is placed beneath the color space graph display area I6. The comment input area I7 is configured to display therein a comment inputted by the user through the keyboard 242 (see FIG. 2). The comment displayed in the comment input area I7 is transmitted to the server together with the image data of the first and second images when the transmission button B5 is clicked. The comment is used to convey, to the developer, a detailed requirement not to be expressed only with the image data, such as "so that blood vessel can be observed more clearly." The developer creates the updating program for updating the program and parameters in consideration of the comment.

As described above, according to the present embodiment, the user can perform respective image adjustments for different areas in the image taken by the electronic endoscope 100, and convey the result after the image adjustments to the developer via the server 300. Thereby, the developer can create the program and parameters on which the user's requirements are more reflected.

In the present embodiment, by mainly operating the keyboard 242 and mouse 244, various operations are carried out. However, alternatively, the various operations may be carried out by operating the footswitch 266, touch panel 216b, and operating buttons 105 of the electronic endoscope 100. For example, in the present embodiment, the specific key of the keyboard 242 (see FIG. 2) is pressed so as to display the log-in screen image (see FIG. 3). However, alternatively, the footswitch 246 may be set ON, or a predetermined operation may be given on the touch panel 216b so as to display the log-in screen image. Furthermore, in the present embodiment, the textual information (for example, the comment displayed in the comment input area I7 on the customizing screen image shown in FIG. 5) is inputted by operating the keyboard 242. However, for instance, the textual information may be inputted through a sound input. Additionally, there may be possible such a configuration that the user can change what kind of function is assigned to each of the keyboard 242, mouse 244, foot switch 246, touch panel 216b, and the operating buttons 105 of the electronic endoscope 100 as required.

The present disclosure relates to the subject matter contained in Japanese Patent Application No. P2007-037617, filed on Feb. 19, 2007, which is expressly incorporated herein by reference in its entirety.

What is claimed is:

1. An electronic endoscope system, comprising:
   an electronic endoscope configured to process an image captured thereby so as to generate a first image with a first image processing tool;
   a network;
   a processor for the electronic endoscope connected with the electronic endoscope and network, the processor being configured to process the first image generated by the electronic endoscope; and
   a server configured to perform data communication with the processor via the network,
   wherein the processor for the electronic endoscope comprises:
      an area specifying unit configured to specify an area to be adjusted in the first image generated by the electronic endoscope;
      an image adjustment unit configured to provide image adjustment for the area in the first image that is specified by the area specifying unit so as to generate a second image with a second image processing tool;
      a request creating unit configured to create update request data including the second image data and positional information representing a position of the specified area in the first image;
      a request sending unit configured to send, to the server, the update request data created by the request creating unit;

an updating data receiving unit configured to receive, from the server, updating data for updating at least one of the first and second image processing tools; and an updating unit configured to update at least one of the first and second image processing tools based on the updating data received by the updating data receiving unit, and wherein the server comprises:

a request receiving unit configured to receive the update request data sent by the request sending unit; and an updating data sending unit configured to send, to the processor, the updating data created based on the update request data received by the request receiving unit.

2. The electronic endoscope system according to claim 1, wherein the processor further comprises:

a display unit;

a first display control unit configured to control the display unit to display thereon the first image generated by the electronic endoscope; and a second display control unit configured to control the display unit to display thereon the second image generated by the image adjustment unit.

3. The electronic endoscope system according to claim 1, wherein the processor further comprises an input unit configured to accept an external input, and wherein the area specifying unit specifies the area to be adjusted in the first image based on the external input accepted by the input unit.

4. The electronic endoscope system according to claim 1, wherein the processor further comprises an input unit configured to accept data inputted therethrough, and wherein the image adjustment unit provides the image adjustment for the specified area in the first image based on the data inputted through the input unit.

5. The electronic endoscope system according to claim 1, wherein the area specifying unit specifies a plurality of areas to be adjusted in the first image, and wherein the image adjustment unit provides different image adjustments for the plurality of areas in the first image that are specified by the area specifying unit, respectively.

6. The electronic endoscope system according to claim 1, wherein the first image processing tool includes a program and parameter employed in the program that are used by the electronic endoscope, and wherein the second image processing tool includes a program and parameter employed in the program that are used by the image adjustment unit of the processor.

7. The electronic endoscope system according to claim 1, wherein the processor further comprises a textual information input unit configured to accept an input of textual information, and wherein the update request data includes the textual information accepted by the textual information input unit.

8. The electronic endoscope system according to claim 1, wherein the network includes an Internet.

9. The electronic endoscope system according to claim 1, wherein the processor further comprises:

a certification information input unit configured to accept an input of certification information;

a certificate information sending unit configured to send the certification information accepted by the certification information input unit, before the request sending unit sends the update request data; and a success notification receiving unit configured to receive, from the server, a successful certification notification issued when certification with the certification information sent by the certification information sending unit is successful, wherein the server further comprises:

a certification information receiving unit configured to receive the certificate information sent by the certificate information sending unit of the processor;

a certificating unit configured to implement the certification with the certification information received by the certification information receiving unit; and a success notification issuing unit configured to issue, to the processor, the successful certification notification when the certification with the certification information received by the certification information receiving unit is successful, and wherein the request sending unit of the processor sends the update request data to the server in response to receiving the successful certification notification.

10. A processor for an electronic endoscope, which is connectable with the electronic endoscope and configured to perform data communication with an external device via a network, comprising:

an area specifying unit configured to specify an area to be adjusted in a first image generated with a first image processing tool by the electronic endoscope;

an image adjustment unit configured to provide image adjustment for the area in the first image that is specified by the area specifying unit so as to generate a second image with a second image processing tool;

a request creating unit configured to create update request data including the second image data and positional information representing a position of the specified area in the first image;

a request sending unit configured to send, to the external device, the update request data created by the request creating unit;

an updating data receiving unit configured to receive, from the external device, updating data for updating at least one of the first and second image processing tools; and an updating unit configured to update at least one of the first and second image processing tools based on the updating data received by the updating data receiving unit.

11. The processor according to claim 10, further comprising:

a display unit;

a first display control unit configured to control the display unit to display thereon the first image generated by the electronic endoscope; and a second display control unit configured to control the display unit to display thereon the second image generated by the image adjustment unit.

12. The processor according to claim 10, further comprising an input unit configured to accept an external input, wherein the area specifying unit specifies the area to be adjusted in the first image based on the external input accepted by the input unit.

13. The processor according to claim 10, further comprising an input unit configured to accept data inputted therethrough, wherein the image adjustment unit provides the image adjustments for the specified area in the first image based on the data inputted through the input unit.

14. The processor according to claim 10, wherein the area specifying unit specifies a plurality of areas to be adjusted in the first image, and wherein the image adjustment unit provides different image adjustments for the plurality of areas in the first image that are specified by the area specifying unit, respectively.

15. The processor according to claim 10, wherein the first image processing tool includes a program and parameter employed in the program that are used by the electronic endoscope, and wherein the second image processing tool includes a program and parameter employed in the program that are used by the image adjustment unit of the processor.

16. The processor according to claim 10, further comprising a textual information input unit configured to accept an input of textual information, wherein the update request data includes the textual information accepted by the textual information input unit.

17. The processor according to claim 10, further comprising:

a certification information input unit configured to accept an input of certification information;

a certificate information sending unit configured to send, to the external device, the certification information accepted by the certification information input unit, before the request sending unit sends the update request data; and a success notification receiving unit configured to receive a successful certification notification issued by the external device when certification with the certification information sent by the certification information sending unit is successful, wherein the request sending unit sends the update request data to the external device in response to receiving the successful certification notification.

* * * * *